United States Patent
Walsh

(10) Patent No.: US 7,351,216 B2
(45) Date of Patent: Apr. 1, 2008

(54) METHOD AND APPARATUS FOR MINIMIZING BED SORES AND LOWER BACK PAIN IN SPINAL INJURY PATIENTS

(75) Inventor: Andrew C. Walsh, 41 Applegate La., Falmouth Foreside, ME (US) 04105

(73) Assignee: Andrew C. Walsh, Falmouth Foreside, ME (US)

( * ) Notice: Subject to any disclaimer, the term of this patent is extended or adjusted under 35 U.S.C. 154(b) by 355 days.

(21) Appl. No.: 11/045,598

(22) Filed: Jan. 26, 2005

(65) Prior Publication Data

US 2006/0167397 A1    Jul. 27, 2006

(51) Int. Cl.
*A61F 5/00* (2006.01)
*A61F 5/37* (2006.01)
*A61G 15/00* (2006.01)
*A47C 17/86* (2006.01)
*A47C 20/02* (2006.01)

(52) U.S. Cl. ............... 602/33; 602/4; 602/5; 602/6; 602/32; 602/34; 602/35; 602/36; 602/38; 602/39; 602/40; 128/845; 128/882; 5/648; 5/649; 5/650; 5/651

(58) Field of Classification Search ........... 602/32–36, 602/38–40, 4–6; 128/845, 882; 5/648–651
See application file for complete search history.

(56) References Cited

U.S. PATENT DOCUMENTS

| 4,621,625 A | * | 11/1986 | Powlan | 602/33 |
| 4,664,099 A | * | 5/1987 | Pearl, Jr. | 602/35 |
| 4,768,834 A | | 9/1988 | Walsh | |
| 4,809,687 A | * | 3/1989 | Allen | 602/4 |
| 4,981,307 A | | 1/1991 | Walsh | |
| 5,509,894 A | * | 4/1996 | Mason et al. | 601/34 |
| 6,238,361 B1 | * | 5/2001 | Poirier | 602/33 |
| 6,349,993 B1 | | 2/2002 | Walsh | |

* cited by examiner

*Primary Examiner*—Patricia Bianco
*Assistant Examiner*—Tarla Patel
(74) *Attorney, Agent, or Firm*—Cesari and McKenna, LLP

(57) ABSTRACT

Apparatus for suspending the calf and foot of a patient recumbent on a bed to relieve pressure on the thigh of the patient includes a leg lift unit in the form of a rigid, trough-like posterior shell shaped to engage under the patient's calf and foot. A bail having opposite ends is connected to the side walls of the shell so that the bail loops above the shell and a support frame extends up and over the bed. A cord hanging from the frame is releasably connected to the bail. By appropriately adjusting the position of the frame, the patient's calf may be subjected to the necessary amount of lift and/or tension to minimize localized pressure on the patient's thigh and buttock areas and to relieve compression forces on the patient's spinal column.

8 Claims, 1 Drawing Sheet

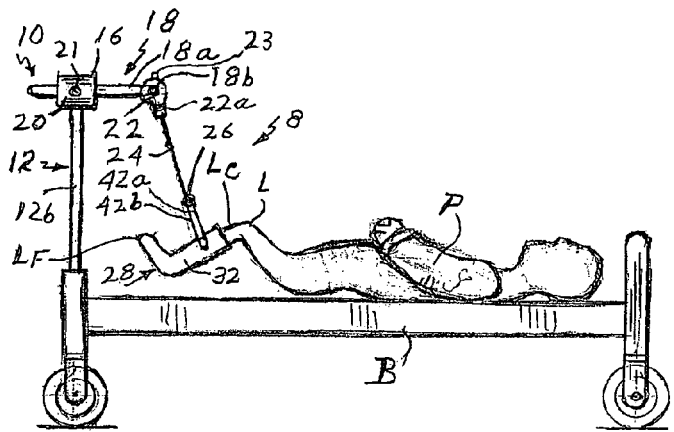
FIG. 1
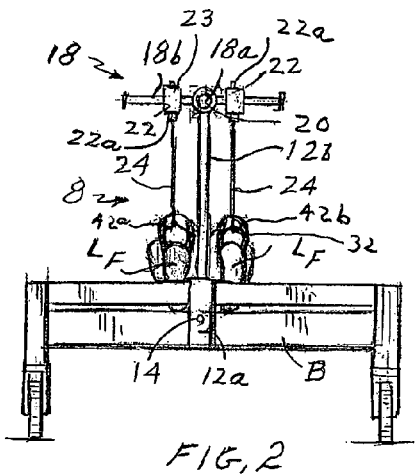
FIG. 2
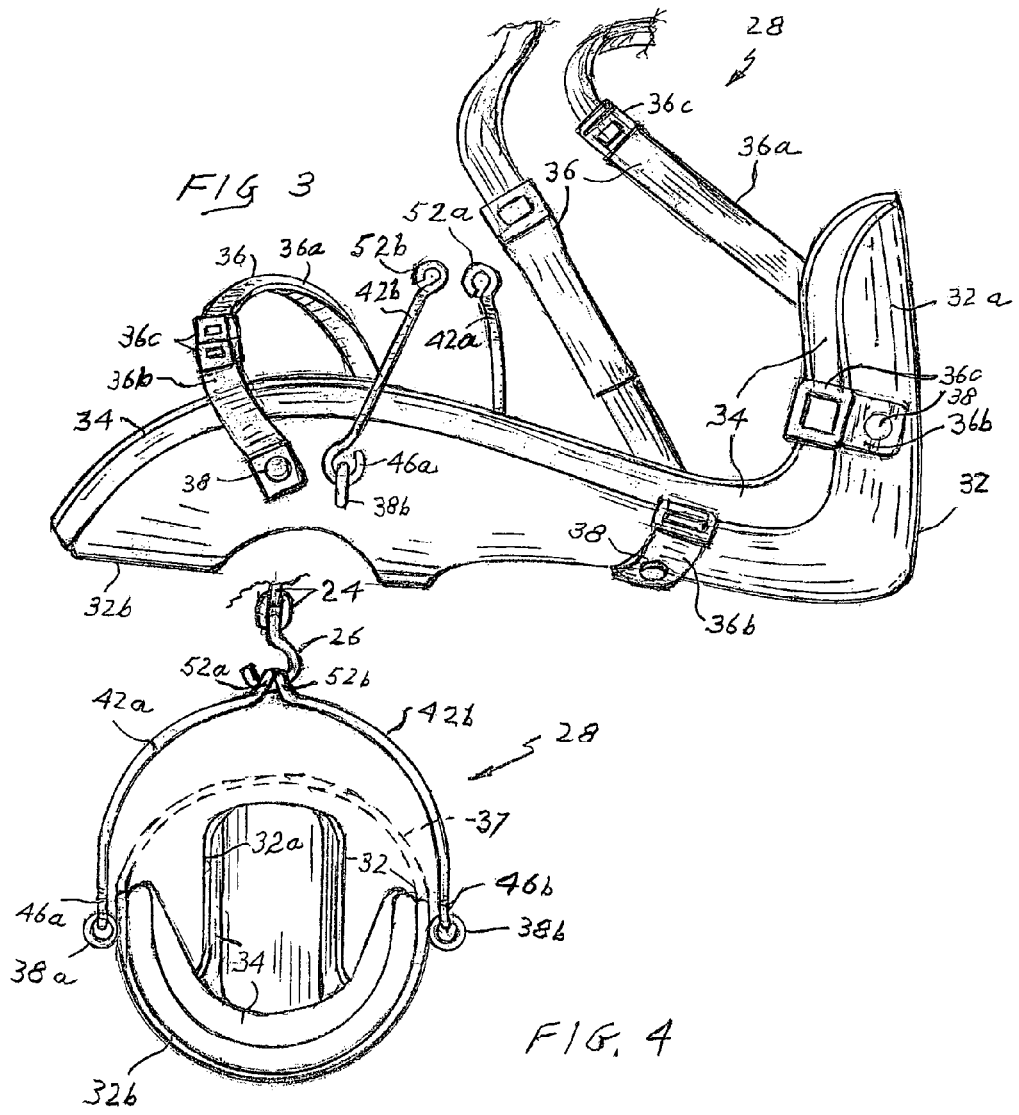
FIG. 3
FIG. 4

METHOD AND APPARATUS FOR MINIMIZING BED SORES AND LOWER BACK PAIN IN SPINAL INJURY PATIENTS

This invention relates to a technique for minimizing bed sores in spinal injury patients. The technique also provides relief to patients suffering chronic lower back pain.

BACKGROUND OF THE INVENTION

Pressure ulcers or bed sores are chronic wounds usually caused by a combination of increased pressure on the affected area and decreased angiogenic response. Pressure ulcers affect almost 10% of people in hospitals, with older people being at highest risk. Various techniques have been employed over the years to prevent and suppress skin breakdown incident to ulcers and bed sores. These techniques include the application of low intensity ultrasound and/or ultraviolet light to the affected area, the use of pressure-relieving mattresses and devices for rotating a patient in his/her bed to minimize localized pressure buildup on the patient's skin which is a prelude to pressure ulcers.

Although these conventional treatment protocols are satisfactory in many respects, they do involve considerable expense. Therefore, they are usually carried out only in hospitals and chronic care facilities.

SUMMARY OF THE INVENTION

Accordingly, the present invention aims to provide an improved method for minimizing the occurrence of pressure ulcers or bed sores.

Another object is to provide such a method which can be practiced at home or wherever else there is a bed supporting a recumbent individual.

Yet another object is to provide apparatus for minimizing the occurrence of decubiti.

Still another object is to provide apparatus of this type which is relatively inexpensive to manufacture.

A further object of the invention is to provide such method and apparatus which are also capable of relieving lower back pain in a recumbent patient.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all as exemplified in following detailed description, and the scope of the invention will be indicated in the claims.

I have devised a unique technique to minimize bed sores and to relieve lower back pain in patients in recumbency. The technique involves the use of suspension apparatus including one or two solid leg lift units of cushioned plastic design with a bail or hanger occupying a mid-anterior region of each unit. Each leg lift unit comprises a single posterior shell or may be split with a posterior shell and an anterior shell in a way to allow the unit to cover substantially the entire calf and foot portions of the patient's leg. The apparatus also includes a frame which may be located at the foot of a bed. The frame has an upright post topped by a horizontal bar which extends out over the bed. A cord or chain extending down from the bar and attached to each leg lift unit via the bail or hanger suspends the associated leg above the bed exerting traction on the thigh. The frame may be adjusted depending upon the degree of pelvic lift and/or traction necessary to relieve the pressure on the patient's thigh(s) and/or spinal column.

BRIEF DESCRIPTION OF THE DRAWINGS

For a fuller understanding of the nature and the objects of the invention, reference may be made to the following detailed description taken in connection with the accompanying drawings, in which:

FIGS. 1 and 2 are diagrammatic side and end views, respectively, of a recumbent patient fitted with apparatus incorporating the present invention;

FIG. 3 is a side elevational view on a much larger scale showing a part of the FIGS. 1 and 2 apparatus in greater detail, and FIG. 4 is a top plan view thereof.

DESCRIPTION OF THE PREFERRED EMBODIMENT

Referring to FIGS. 1 and 2 of the drawings, a patient P is shown recumbent on a bed B. The patient has legs L each including a calf $L_C$ and a foot $L_F$. At least one of the legs L is elevated and subjected to traction by a suspension system indicated generally at 8, the objective being to relieve pressure on the buttock of each elevated leg L. There results, then, a lowering of the pressure on the skin of the patient at the buttock(s) which minimizes the occurrence of pressure ulcers or bed sores thereat. The combined lift/traction exerted on the patient's leg(s) also tensions the patient's spine thereby alleviating any lower back pain suffered by the patient.

Still referring to FIGS. 1 and 2, the system 8 comprises a frame shown generally at 10, including an extensible upright post or stantion 12 having a lower section 12a and an upper section 12b which is telescopically received in the lower section 12a. The position of section 12b relative to section 12a maybe set by suitable means such as a set screw 14 threaded into the side wall of section 12a and bearing against section 12b. The post 12 may be incorporated into the foot of bed B as shown or stand on the floor adjacent to the bed.

The upper end of the post section 12b carries a sleeve 20 which slidably receives the leg 18a of a horizontal T-bar 18 so that the two arms 18b of the T-bar extend out over the bed B. Preferably the legs and arms of T-bar 18 have square crossections. A set screw 21 in sleeve 20 may set the horizontal position of the T-bar 18 so that the arms 18b of T-bar 18 overlie the legs L of patient P on bed B.

Each arm 18b supports a sleeve or slide 22 which is slidable along that arm and each sleeve or slide includes an eye 22a to which is connected the upper end of a chain or cord 24 the lower end of which carries a hook 26 (FIG. 4) which may be hooked to a leg lift unit shown generally at 28. If desired, each sleeve or slide 22 may include a set screw 23 to set its position on the corresponding arm 18b. Thus, frame 10 may be adjusted to suspend one or both legs of patient P above bed B as shown in FIGS. 1 and 2 so as to subject the patient's leg(s) to a selected amount of lift and/or tension.

Refer now to FIGS. 3 and 4 which show the leg lift unit 28 in greater detail. It comprises an L-shaped, rigid plastic posterior shell 32 having a foot section 32a and a calf section 32b. Shell 32 is shaped and dimensioned so that it can engage under the foot $L_C$ and calf $L_F$ of the patient P. Preferably, a resilient pad 34 extends along the inner surfaces of sections 32a and 32b to cushion the patient's leg L.

Leg lift unit 28 may also include a plurality of straps 36 for securing the shell 32 to a patient's leg L. In the illustrated unit, there is a strap 36 near the upper end of the calf section 32b of the shell, a similar strap 36 near the free end of the foot section 32a and a third strap 36 located near the lower end of shell section 32b just above the ankle area. Each strap 36 may comprise a pair of strap sections 36a and 36b, corresponding first ends of those sections being connected to opposite sides of the shell 32 by rivets or pins 38 and corresponding second ends of the sections carrying interlocking clasps or buckles 36c, 36c. Preferably, the length of at least one strap section, 36a or 36b of each strap 36 may be adjusted by changing the position of a clasp 36c along its strap section and fixing that position via Velcro brand hook and loop fasteners incorporated into that section.

In lieu of straps 36, the leg lift unit 28 may include an anterior shell shown in phantom at 37 in FIG. 4, which is hinged to posterior shell 32 in "clam shell" fashion and fits over the foot $L_F$ and calf $L_C$. Thus when the two shells are closed and latched, the unit completely covers the leg L.

As best seen in FIG. 4, a pair of eyes 38a and 38b are mounted to the opposite sides of the calf section 32b of shell 32 near the upper end thereof. Linked to these eyes are the lower ends of a pair of bail sections 42a and 42b which extend up above shell 32. In other words, the lower ends of the bail sections 42a and 42b have eyes 46a and 46b which hook through eyes 38a and 38b, respectively. The bail sections 42a and 42b extend up above shell 32 (and any leg L therein) and their upper ends are terminated by eyes 52a and 52b, respectively, which when the two sections are brought together as shown in FIG. 4, are in register. After eyes 52a and 52b are brought into register, the hook 26 at the lower end of cord or chain 24 (FIGS. 1 and 2) may be hooked through those eyes thereby securing them together forming a single rigid bail or hanger suspended from frame 10 via cord 24 thus enabling the elevated support of the leg lift unit 28 and any leg L therein.

As shown in FIGS. 1 and 2, one or both legs of the patient P, when supported by the suspension system 8 may be elevated and pulled toward the foot of bed B so as to relieve the pressure on the thigh(s) and buttock(s) of patient P and also to exert traction on his/her spinal column. This not only minimizes the occurrence of bed sores in the patient's thigh and buttock areas, but also helps to reduce any lower back pain suffered by the patient.

The elevation of the T-bar 18 may be adjusted via set screw 14 so as to lift the thigh(s) and buttock(s) of patient P entirely from bed B or simply to relieve the pressure on one or both of same. By adjusting the horizontal position of the T-bar arms 18b over bed B via set screw 21, the tension or pulling force on patient's leg L may be adjusted as needed to optimize the treatment of the patient. Also, of course, if both of the patient's legs L are suspended by the system 8, the leg spread may be adjustably fixed by setting the position of sleeves or slides 22 on the T-bar arms 18b via set screws 23.

Preferably, the eyes 38a, 38b are located at least two-thirds of the way up along shell section 32b so that the force transmitted to each leg lift unit 28 via cord 24 does not tend to straighten out the patient's leg L, but rather to raise and tension the thigh sufficiently to lift the patient's buttock partially or entirely from bed B and exert tension on the lower end segment (lumbar) of the patient's spinal column.

It will thus be seen that the objects set forth above, among those made apparent from the preceding description, are efficiently attained. Also, since certain changes may be made in carrying out the above method and in the construction set forth without departing from the scope of the invention, it is intended that all matter contained in the above description or shown in the accompanying drawings shall be interpreted as illustrative and not in a limiting sense.

What is claimed is:

1. Apparatus for suspending the calf and foot of a patient recumbent on a bed to relieve pressure on the thigh and buttock of the patient, said apparatus comprising
   a leg lift unit, said unit including
      a rigid, trough shaped posterior plastic shell having an interior surface shaped to engage under the patient's calf and foot, said shell having opposite side walls and an upper end,
      one or more securements connected to said side walls for securing the shell to the patient's calf and foot, and
      upwardly curved hanger having opposite ends directly connected to said side walls of the shell at least two-thirds of the way up along the shell toward said upper end so that the hanger extends above said shell, and
   a support frame including
      an upright post having an upper end and a lower end for positioning at the foot of the bed,
      a horizontal bar having one end adjustably secured to the upper end of the post and a second end extending over the bed, and
      a single cord having an upper end connected to said bar and a lower end releasably connected to the hanger so that the shell is suspended from the bar solely by the cord and the hanger.

2. The apparatus defined in claim 1 and further including padding covering the interior surface of said posterior shell.

3. The apparatus defined in claim 1 wherein said at least one securement includes a plurality of flexible straps connected to the opposite sides of the shell at spaced apart locations therealong.

4. The apparatus defined in claim 1 wherein said at least one securement includes
   a rigid trough-like anterior shell having an interior surface shaped to engage over the patient's calf and foot, and
   one or more connections releasably connecting the anterior shell to the posterior shell.

5. The apparatus defined in claim 4 and further including padding covering the interior surfaces of the posterior and anterior shells.

6. The apparatus defined in claim 1 wherein said hanger comprises a rigid bail composed of two mirror-image sections, said sections having corresponding first ends pivotally connected to the opposite walls of the posterior shell and corresponding second ends formed as eyes which can be brought into register above the posterior shell.

7. The apparatus defined in claim 6 wherein the lower end of said cord carries a hook which may be hooked through said eyes to secure them together.

8. The apparatus defined in claim 1 wherein said post is composed of telescoping first and second sections and includes first means for adjustably fixing the relative positions of said sections and second means at the upper end of the post for adjustably fixing the horizontal position of said bar relative to the post.

* * * * *